(12) United States Patent
Engelman

(10) Patent No.: US 11,758,971 B2
(45) Date of Patent: Sep. 19, 2023

(54) FOOT ORTHOSIS HAVING SULCUS SUPPORT AND METHODS FOR MAKING SAME

(71) Applicant: Ian Kenton Engelman, Portland, ME (US)

(72) Inventor: Ian Kenton Engelman, Portland, ME (US)

( * ) Notice: Subject to any disclaimer, the term of this patent is extended or adjusted under 35 U.S.C. 154(b) by 208 days.

(21) Appl. No.: 17/235,769

(22) Filed: Apr. 20, 2021

(65) Prior Publication Data

US 2021/0330021 A1    Oct. 28, 2021

Related U.S. Application Data

(60) Provisional application No. 63/015,199, filed on Apr. 24, 2020.

(51) Int. Cl.
| | | |
|---|---|---|
| A43B 7/14 | (2022.01) | |
| A61F 5/01 | (2006.01) | |
| A43B 7/1425 | (2022.01) | |
| A43B 7/1415 | (2022.01) | |

(52) U.S. Cl.
CPC .............. *A43B 7/14* (2013.01); *A43B 7/1415* (2013.01); *A43B 7/1425* (2013.01); *A61F 5/0111* (2013.01)

(58) Field of Classification Search
CPC ......... A43B 7/14; A43B 7/1425; A43B 7/145; A43B 7/1415; A61F 5/019; A61F 5/0195; A61F 5/0111; A61F 5/0127
USPC ......................................................... 36/140
See application file for complete search history.

(56) References Cited

U.S. PATENT DOCUMENTS

| | | | | |
|---|---|---|---|---|
| 1,730,466 | A * | 10/1929 | Mallott | A43B 7/145 36/44 |
| 1,787,398 | A * | 12/1930 | Sidgreaves | A61F 5/019 602/30 |
| 2,681,515 | A * | 6/1954 | Frese, Jr. | A43B 7/22 36/178 |
| 2,862,313 | A * | 12/1958 | Jones | A43B 7/1435 36/145 |
| 6,090,059 | A * | 7/2000 | Wasserman | A61F 5/0111 602/23 |
| D513,838 | S | 1/2006 | Birkenstock | |
| D514,779 | S | 2/2006 | Birkenstock | |
| D532,586 | S | 11/2006 | Birkenstock | |
| 2002/0056209 | A1* | 5/2002 | Clough | A43B 7/145 36/142 |

(Continued)

OTHER PUBLICATIONS

"Silipos Felt Hammer Toe Crest", downloaded from https://silipos.com/products/felt-hammer-toe-crest on May 17, 2021.

*Primary Examiner* — Marie D Bays
(74) *Attorney, Agent, or Firm* — Shalom Wertsberger; Saltamar Innovations

(57) ABSTRACT

A foot orthotic designed to unweight the ball of the foot, or more precisely the foot region of one or more of the five metatarsal heads, to alleviate pain while walking or standing. Using a connector from the foot orthotic to a sulcus bar provides a reproduceable front to back position of the sulcus bar relative to the foot orthotic. In certain aspects of the invention the connector provides further unweighting of the metatarsal heads, and also ensures a specific custom position of the sulcus bar throughout the foot orthotic fabrication process. Various methods of manufacturing an orthotic are also disclosed.

7 Claims, 6 Drawing Sheets

(56) References Cited

U.S. PATENT DOCUMENTS

| | | | | |
|---|---|---|---|---|
| 2006/0254092 | A1* | 11/2006 | Stevens | A43B 7/26 |
| | | | | 36/71 |
| 2010/0018078 | A1* | 1/2010 | Bobbett | A43B 3/107 |
| | | | | 36/88 |
| 2010/0251568 | A1* | 10/2010 | Haruda | A43B 17/102 |
| | | | | 36/43 |
| 2010/0269371 | A1* | 10/2010 | Gray | A43B 7/141 |
| | | | | 36/43 |
| 2014/0068967 | A1* | 3/2014 | Jones | A43B 17/00 |
| | | | | 36/43 |
| 2014/0213954 | A1* | 7/2014 | Roth | A61F 5/019 |
| | | | | 602/30 |
| 2015/0264998 | A1* | 9/2015 | Berggren | A43B 7/149 |
| | | | | 36/31 |
| 2019/0313731 | A1* | 10/2019 | Dwyer | A43B 7/1445 |
| 2019/0365026 | A1* | 12/2019 | Clough | A43B 7/149 |
| 2020/0170340 | A1* | 6/2020 | Kim | A43D 25/10 |
| 2021/0030113 | A1* | 2/2021 | Schuster | A43B 7/26 |
| 2021/0112920 | A1* | 4/2021 | Dinshaw | B33Y 80/00 |
| 2021/0274885 | A1* | 9/2021 | Billah | A43B 7/144 |
| 2021/0289881 | A1* | 9/2021 | Sugawara | A43B 7/149 |
| 2022/0039517 | A1* | 2/2022 | Kang | A43B 7/1475 |

* cited by examiner

FOOT ORTHOSIS HAVING SULCUS SUPPORT AND METHODS FOR MAKING SAME

FIELD OF THE INVENTION

The present invention relates generally to orthotic foot supports and more particularly to a foot orthotic which provides support for the foot at the sulcus and/or between the metatarsal heads.

BACKGROUND OF THE INVENTION

The human foot is colloquially divided into the heel area, the arch area, the ball area and the toes. More precisely the bones in the posterior portion of the foot are known as the calcaneus which generally forms the heel area and the talus bone located above it. The arch area comprises five bones namely the cuboid, navicular, and three cuneiform bones. Together, those seven bones are known as the tarsus. Five elongated metatarsal bones are coupled to the tarsus by joints named the tarsometatarsal joints. Each of the metatarsal bones is coupled in turn to 'toe bones' respectively, the toe bones are named phalanges and each phalange is coupled to the respective metatarsal head by a proximal phalanx. The first toe, known colloquially as the great toe, has two phalanges, and each of the other four toes has three phalanges.

Each metatarsal bone is commonly conceptually divided to three parts: the end closest to the ankle is named the tarsal extremity, and commonly referred to as the base, the end closest to the toe is named the phalangeal extremity and commonly referred to as the head, and the bone shaft connecting the two extremities which is commonly referred to as the body. The foot bones articulate and are connected together by ligaments and muscles.

The area immediately distal to where the metatarsal heads join the respective phalanges is referred to in these specification as the Sulcus or equivalently the foot sulcus. This area generally extends laterally from the inside to the outside of the foot, and is characterized by a groove (Sulcus-Latin) elevated from the lower surface of the foot. The sulcus is generally defined by the tissue that underlies the proximal phalanxes and distal to the metatarsal heads. A generally accepted term in the art, the Sulcus is a crescent shaped area under the proximal phalanxes extending medially and laterally the width of the foot under the four web spaces.

The tissue separating the metatarsal heads from weight bearing surface, such as a floor, is generally thin. Since the metatarsal heads area is under heavy stress during normal walking and standing, and as the thin tissue provides relatively low shock absorption, the metatarsal area is commonly a source of pain, especially as the human weight increases and more so after a lifetime of walking on the unforgiving flat, hard surfaces that modern humans endure.

Unweighting the metatarsal heads area is often desired in the art of foot orthotic design. The term 'unweighting' relates to reducing the force applied to a target area of the anatomy by the equal and opposite reaction force from a person's mass imparted to an external surface such as a floor or the inside bottom surface of the shoe. In this specification, the target area of the anatomy is generally the metatarsal heads and the force acting thereupon are commonly known as the ground reaction force. A common goal of foot orthotic design is redistributing the ground reaction force to more pressure tolerant areas on the bottom of the foot. By redistributing the ground reaction force operative on the metatarsal heads to the shafts of the metatarsals, just proximal to the metatarsal heads, pressure is reduced on the metatarsal heads. Such force redistribution is achieved with a metatarsal pad. Reducing the upward ground reaction forces directed just below the boney prominences of the metatarsal heads is often a clinical priority for pain reduction.

A metatarsal pad is a known device aiming to alleviate the pressure in the metatarsal heads area. A metatarsal pad is positioned below the foot and proximally relative to the metatarsal heads, or stated differently just behind the metatarsal heads in the direction of the ankle. When placed correctly such metatarsal pad partially—yet oftentimes insufficiently—unweights the metatarsal heads. The shortcoming of the metatarsal pad stem from the fact that it provides support only from one side of the metatarsal heads, namely the proximal side.

It is seen therefore that there is a clear, yet heretofore unmet need for orthotic devices and improved methods to further redirect metatarsal heads ground reaction forces to unweight the metatarsal heads region of the human foot in general, and more specifically to effectively redirect at least a portion of the ground reaction forces to portion of the foot distal to the metatarsal heads, and between the metatarsal heads. Furthermore, there is a clear need for a simple to perform method of manufacturing such orthotic device while maintaining precise alignment between various portions thereof.

SUMMARY OF THE INVENTION

In order to overcome the shortcomings of the prior art, in its simplest form, aspects of the present invention provides support for the metatarsal heads area of a foot on its distal side, i.e. the side which is farther away from the heel, by providing a foot orthotic having an integral sulcus bar. Some embodiments of the invention provide support for the metatarsal heads area on the lateral, and/or medial sides, optionally including areas between the metatarsal heads, in addition to or instead of, the metatarsal heads distal side. This support is obtained by utilizing an orthotic which provides a sulcus bar under the patients' foot sulcus area, the bar is coupled to the orthotic front trimline of an orthotic main body via at least one connector. The sulcus bar is sufficiently high so as to transfer at least some of the ground reaction force applied to the foot during standing and/or walking, to the soft tissues of the foot sulcus, the intermetatarsal soft tissue or to soft tissue on either side of the metatarsal heads region. As well as having sufficient height, the anterior/posterior placement of the sulcus support bar will substantially change its effectiveness; aspects of the invention provide precise anterior/posterior disposition of the sulcus bar. A full sulcus support bar extends between the lateral and medial sides of the foot, however different sections of the sulcus support bar may be omitted. The sulcus support bar extends upwardly from the orthotic operational lower surface towards the patients' foot. Thus, the sulcus support bar advantageously unweights the metatarsal heads. It is noted that the most influential unweighting of the metatarsal heads is achieved by unweighting the inferior boney prominences of the metatarsal heads. Other aspects of the invention provide methods of manufacturing for an orthosis with integral sulcus bar while maintain precise geometrical relationship between different portions thereof, such as the distance and orientation of the sulcus support bar relative to the orthotic main body and/or to the connector bar(s). Notably, the geometrical relationship is considered as a planar geometrical relationship projected on the X-Y plane when the orthotic is at rest, while operationally, the spatial relationship may change in response to gait forces.

For brevity the sulcus support bar shall be equivalently termed the sulcus bar.

When the orthotic is used to support the patient's foot from the surface carrying the patient during walking, standing and the like, the orthotic is said to be 'operational', and thus a description of an element disposition or relationship as operational or operationally implies that the referenced condition exists during operation of the orthotic, or stated differently, during such times when the orthotic is worn and providing support to the patients' foot or portions thereof.

A person skilled in the art would readily understand that the foot orthotic is constructed and dimensioned to generally fit under, and substantially corresponds to, the patient's foot, such that the heel portion generally underlies the foot heel, the midfoot portion generally underlies the midfoot region, the forefoot portion orthotic front trimline generally underlies an area between the metatarsal heads and the midfoot, and the sulcus support bar generally laterally underlie at least a portion of the foot sulcus corresponding to at least one proximal phalanx or a lateral portion thereof. However, various relations between the orthotic and portions thereof and a patient's foot and portions thereof, describe the desired respective positioning of the relevant portions when the orthotic is operational. The skilled in the art would readily understand that in order to function properly the orthotic should be naturally aligned with the foot in general correspondence between intended portions thereof, however the correspondence between the foot and the orthotic may be imprecise. Such minor imprecision should not be construed as failure of the invention or the orthotic.

Maintaining stable positioning of the sulcus bar relative to the orthotic, and thus to the patients' foot during fabrication and/or use presents a significant challenge to the skilled in the art. Various embodiments and aspects of the present invention achieve positional stability between the forefoot section of the orthotic and the sulcus bar. As such front to back stability is challenging to the orthotic fabricator, and aspects of the invention provide significant and novel advantages to users and/or fabricators of such orthotics.

Operationally the orthotic is maintained in generally predetermined position under the foot by additional components which are not shown, most commonly, a shoe. Other possible components are an orthopedic walking boot, a foot and ankle brace; it's possible to maintain position with one or more straps, a bandage, cast, and the like.

An aspect of the invention provides an orthotic for a patient's foot comprising a body portion having a top side and a bottom side, the orthotic may be conceptually and/or physically divided into a heel portion, and a midfoot portion coupled to and extending distally from the heel portion. The midfoot portion extends to a forefoot portion having an edge, colloquially referred to as an orthotic front trimline. At least one sulcus bar connector having an elongated body with a first and second end zones where the first end zone is coupled to the forefoot portion, and the second end zone extending distally therefrom, for coupling a sulcus support bar to the forefoot portion. The sulcus bar is coupled to the second end zone of the connector and extending medially and or laterally therefrom to generally fit under the patients' foot sulcus or a portion thereof, the sulcus bar extends sufficiently upwardly towards the foot sulcus to exert a portion of a ground reaction force to the sulcus or a portion thereof.

Stated differently, the forefoot region terminates lengthwise just before the metatarsal heads and the sulcus support bar lies after the metatarsal heads, as viewed from the heel. The sulcus support bar extends upwardly towards the foot and into the foot sulcus so as to support the part of a respective metatarsal head or heads farther from the heel. It is not recommended to provide support directly under the metatarsal heads, but it is advantageous to apply the support to the respective phalanxes. The sulcus support bar extends laterally to underlie at least one of the proximal phalanxes, i.e. the toe bone or the portion thereof closest to the respective metatarsal head of at least one toe. However, it is common for the sulcus support bar to extend below a plurality, and optionally all, of the toes, to provide support to all the metatarsal heads. The sulcus bar connector provides locational stability at least during fabrication to maintain the sulcus support bar in the most desirable position ahead of the metatarsal heads, and under the sulcus. It is noted that utilizing a sulcus bar connector affords a design which results in consistent and reproducible positioning, mostly in the proximal-distal direction of the sulcus bar when the orthotic is worn and between different orthoses. Furthermore, in certain embodiments the sulcus bar connector is extended upwardly sufficiently to provide support to the foot portion adjacent to it, namely to the area about the lateral and/or medial side of the foot, and/or the respective intermetatarsal head region. Various embodiments of the invention utilize one or more sulcus bar connector, therefore one or more of the connector(s) may be extend upwardly. Thus, in certain embodiments a sulcus bar connector disposed between any two metatarsal heads is extended sufficiently upwardly towards the intermetatarsal area of the respective metatarsal heads to exert a portion of the ground reaction force thereto. Similarly in certain embodiments, a sulcus bar connector disposed on the medial side of the first metatarsal head is extended upwardly to exert a portion of a ground reaction force to the respective medial area about the first metatarsal head. Similarly in certain embodiments, a sulcus bar connector disposed on the lateral side of the fifth metatarsal head is extended upwardly to exert a portion of a ground reaction force to the respective lateral area about the fifth metatarsal head. In certain embodiments the sulcus bar connector is used during manufacturing and is then discarded after the geometrical relations between the sulcus bar and the orthotic body is otherwise maintained, such as, by way of example affixing the sulcus bar to the orthotic body by an underlayment layer disposed below the body, by a cover that covers both the sulcus bar and the orthotic body or portions thereof, or both. A cover overlying the orthotic shall be equivalently referred to herein as a topcover.

Therefore, optionally in certain embodiments the sulcus bar connector extends sufficiently upwardly towards the foot to exert a portion of a ground reaction force to the respective area of the foot adjacent thereto. Further optionally the orthotic comprises a plurality of sulcus bar connectors and at least of the plurality of connectors extends sufficiently upwardly towards the foot to exert a portion of a ground reaction force to the respective area of the foot adjacent thereto.

The main orthotic body is defined by trimlines, and the orthotic body front trimline is the trimline operationally disposed proximally to the metatarsal heads. Stated differently the portion of the trimline of the orthotic body disposed closer to the metatarsal heads, and under the forefoot, is the front trimline. The orthotic body front trimline shall be equivalently referred to as the "front trimline".

The midfoot support may optionally arch upwardly to provide support to the portion of the foot known as the longitudinal arch.

In some embodiments the sulcus bar connector is disposed to lie between two metatarsal heads. Such connector is referred to as an inter-metatarsal connector. By way of example the inter-metatarsal connector may lie between the first and second metatarsal heads of the patient's foot, when the orthotic is operational. However, an inter-metatarsal connector may lie between any two adjacent metatarsal heads.

In certain embodiments the sulcus bar connector is embodied by a side connector for coupling the sulcus bar to the forefoot portion of the orthotic. Operationally, a side connector extends along a side of the foot, at least along the portion between the forefoot and the sulcus and is coupled to the forefoot on a first end thereof and to the sulcus bar on a second end thereof. in certain embodiments a side connector may extend on the medial side or the lateral side of the foot, and a lateral and/or medial side connectors may be utilized together or separately in different embodiments, and/or in any combination with one or more intermetatarsal connectors. In certain aspects of the invention the side connector is utilized only during manufacturing and is removed afterwards, in which case the side connector is considered a temporary fixator.

A single sulcus bar connector, or a plurality thereof may be utilized in various embodiments of the invention, and the number, disposition, and type of sulcus bar connectors may be mixed as desired to achieve a desired anatomical correction and/or patient comfort. Certain patients benefit from improved placement of the phalanxes and the metatarsal heads by utilizing inter-metatarsal sulcus bar connector, while others may find side or recessed sub-metatarsal connectors more comfortable. Thus, the selection of the type of the sulcus bar connector is a matter of technical choice, and preferably an individualized choice. Optionally the connectors provide upward support between the metatarsal heads which reduces the pressure directly under the metatarsal heads. To that end, as described above, in certain embodiments one or more of the connectors may extend sufficiently upwardly to transfer at least a portion of the ground forces to the respective foot region against which they lie.

The sulcus bar connector may be flexible in a longitudinal direction so that it allows for dorsiflexion of the toes during heel off, which is a part of ambulation late in stance phase. There may be circumstances and conditions such as sesamoiditis where a stiffer version of the connector bar would be desirable in order to limit motion. Additionally, the medial/lateral position of the connector will determine its effectiveness. It's most desirable to locate the connector bar perfectly in between the metatarsal heads, but effective unweighting can occur without a perfectly positioned connector. It would not be desirable, however, for the connector bar to reside under the metatarsal head, in full or in part. The term "flexible in a longitudinal direction" implies that the sulcus connector bar may operationally arch at least along its longitudinal axis, to allow the X-Y plane of the sulcus support bar to form an angle with the X-Y plane of the orthosis body during dorsiflexion of the toes.

Optionally at least a first portion of the sulcus bar has a different height than a second portion of the sulcus bar. Further optionally at least a first portion of the sulcus bar has a different width in the proximal-distal direction than at least a second portion thereof. Stated differently, varying portions of the sulcus bar may be of varying dimensions. Thus, by way of example the portion of the sulcus bar distal to the first metatarsal head may extend more upwardly, and/or be wider than, a portion of sulcus bar at an area distal to another metatarsal head. Varying cross-section of the sulcus bar or portions thereof may be utilized. Furthermore varying cross sections may be utilized between one or more of sulcus bar connectors when a plurality of sulcus connectors are utilized, and individual portions of each sulcus bar connector may also utilize varying cross sections. Such cross-section variations may be continuous or stepwise.

Optionally, in certain embodiments the orthotic further comprises a metatarsal pad disposed adjacent to, or extending to, the front trimline of the orthotic body, i.e. at the at forefoot portion close to the proximal side of the metatarsal heads. This allows support of the metatarsal heads from both distal and proximal directions providing further protection to the boney prominences of the metatarsal heads.

Optionally at least a portion of the orthotic is covered with an energy absorptive material, such as a foam layer, a fabric layer, or any other resilient covering in order to provide softer interface between the foot or portions thereof and the orthotic.

The orthotic body or at least a portion thereof may comprise a rigid material or a semi rigid material.

Addition of a metatarsal pad extending to, or adjacent to, the orthotic front trimline of the forefoot portion, is explicitly considered as an option in all aspects and embodiments of the invention.

Optionally the orthotic or portions thereof is manufactured utilizing one or more additive printing processes.

In yet another aspect of the invention there is provided a method of making an orthotic comprising manufacturing an orthotic, or at least a portion of the orthotic as described herein utilizing an additive manufacturing process, colloquially known as 3D printing. The method comprises obtaining three-dimensional model of a patient's foot, selecting an orthotic geometry to provide support to at least one metatarsal head of the foot, and forming the orthotic in accordance with the selected geometry utilizing an additive printing process. Optionally the manufacturing process further comprises trimming and dressing the orthotic, such as removal of spurious portions, coating of the orthotic, attaching the orthotic to a substrate acting as a bottom support, applying aesthetic additions, and the like.

Such manufacturing process allows a definitive anterior/posterior positioning of the sulcus par. This advantage leads to easy manufacturing and improved fitting of the orthotic to an individual patient's specific foot anatomy.

Yet another orthosis manufacturing process embodiment utilizes at least one temporary fixator. The process comprising obtaining an orthosis body geometry, a sulcus bar geometry and a spatial relationship therebetween, adding at least one temporary fixator extending between the orthosis body and the sulcus bar, such that the fixator disposes the sulcus bar at a predetermined spatial distance and orientation relative to the orthosis body. After the geometry of the assembly of assembly is determined, manufacturing at least a portion of the orthotic body, the sulcus bar, and the fixator or fixators, affixing the geometrical relationship between the orthotic body and the sulcus bar, and trimming at least a portion of the fixator. Affixing the geometrical relationship between the orthotic body and the sulcus bar may be performed by coating at least one side of the orthotic body and the sulcus bar with a topcover made of energy absorptive material, affixing the orthotic and the sulcus bar to a bottom underlayment support acting as a substrate, or both. In certain embodiments the process further includes trimming the energy absorptive material to a desired size. Optionally the energy abortive material is a polymeric foam. Optionally both sides of the orthosis body and the sulcus bar are coated with the energy absorbing material. The optional substrate may be an inner portion of shoe sole, a flat surface that forms a lower insole body, and the like. The bottom support may be formed of energy absorptive material, and in certain embodiments a top and bottom sheets of such material are adhered to the top and the bottom of the orthotic, respectively.

Notably, embodiments and aspects of the present invention may utilize additive manufacturing processes to manufacture at least a portion of the orthotic described hereinabove.

SHORT DESCRIPTION OF DRAWINGS

The summary above, and the following detailed description will be better understood in view of the enclosed drawings which depict details of preferred embodiments. It should however be noted that the invention is not limited to the precise arrangement shown in the drawings and that the drawings are provided merely as examples.

Figure 7A:
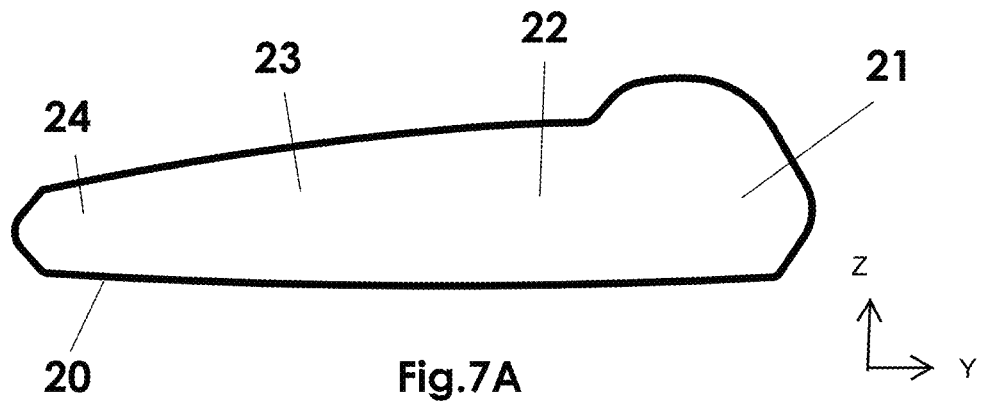
Figure 7B:
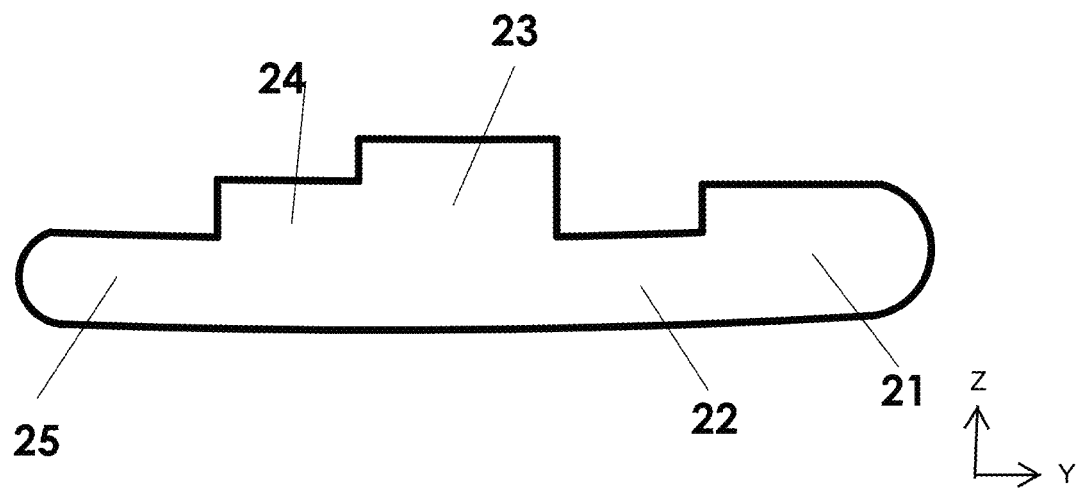
Figure 8:
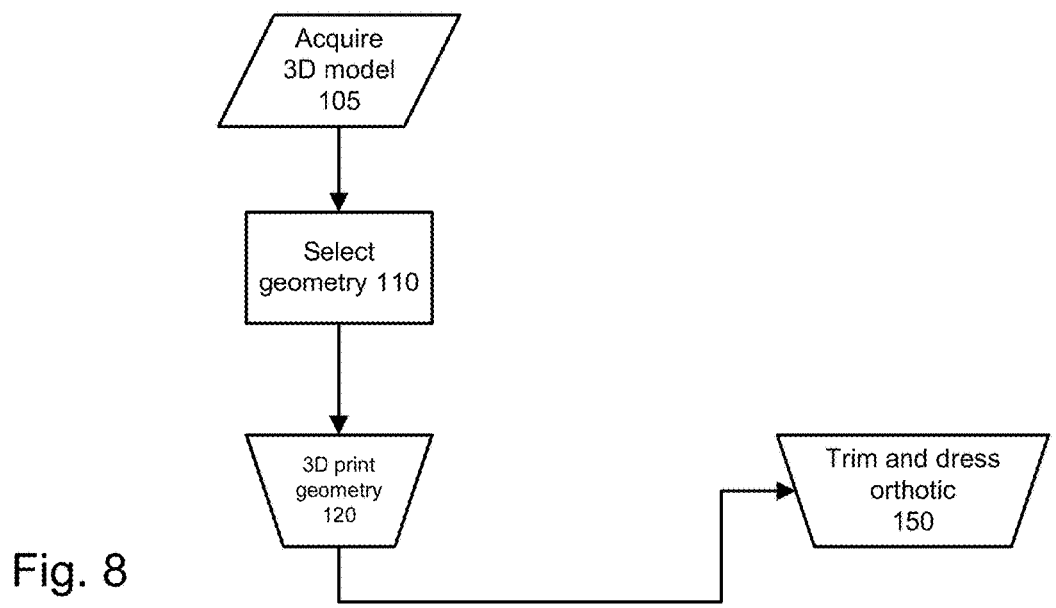
Figure 8A:
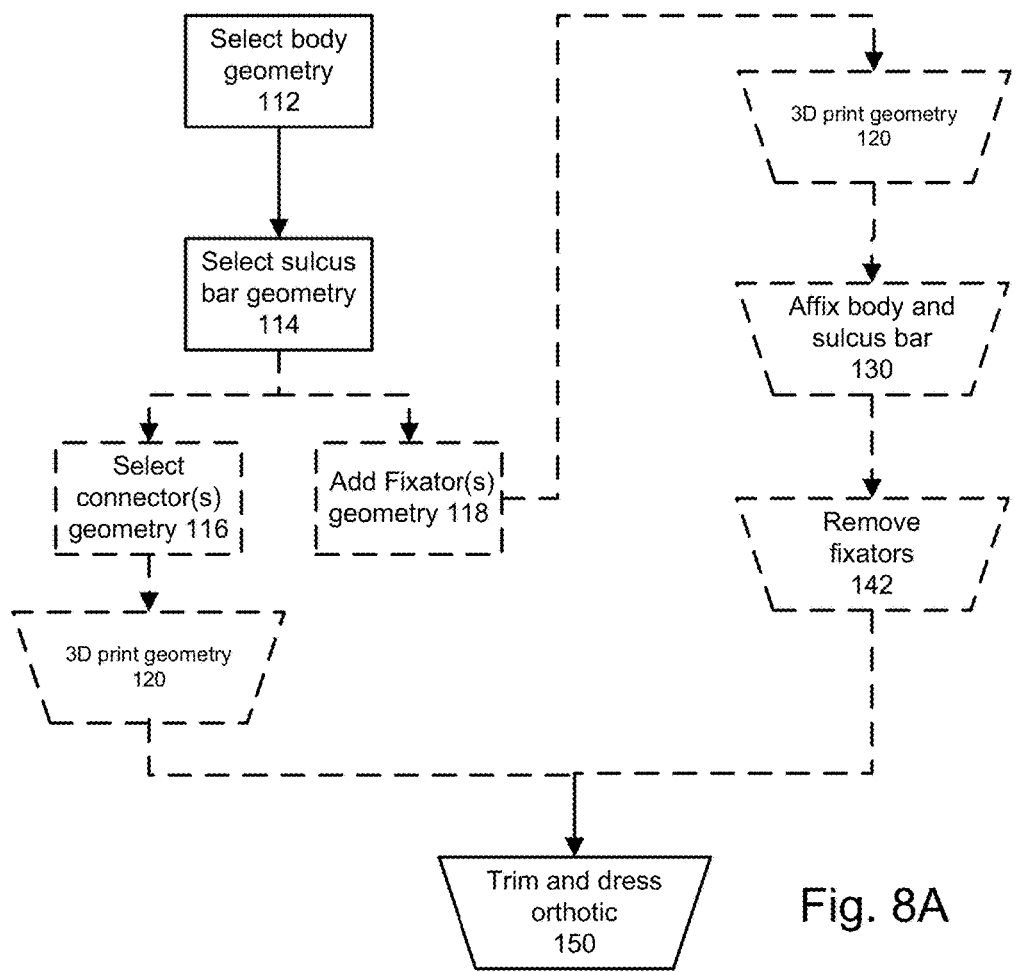

FIG. 7A depicts a simplified front view of a sulcus bar with varying heights. FIG. 7B depicts a simplified view of a sulcus bar with optional stepwise height variations FIG. 8 is a simplified block diagram of a method for producing an orthotic comprising a sulcus bar. FIG. 8A is a simplified flow diagram of certain portions of FIG. 8, and depicts additional optional steps.

Figure 9A:
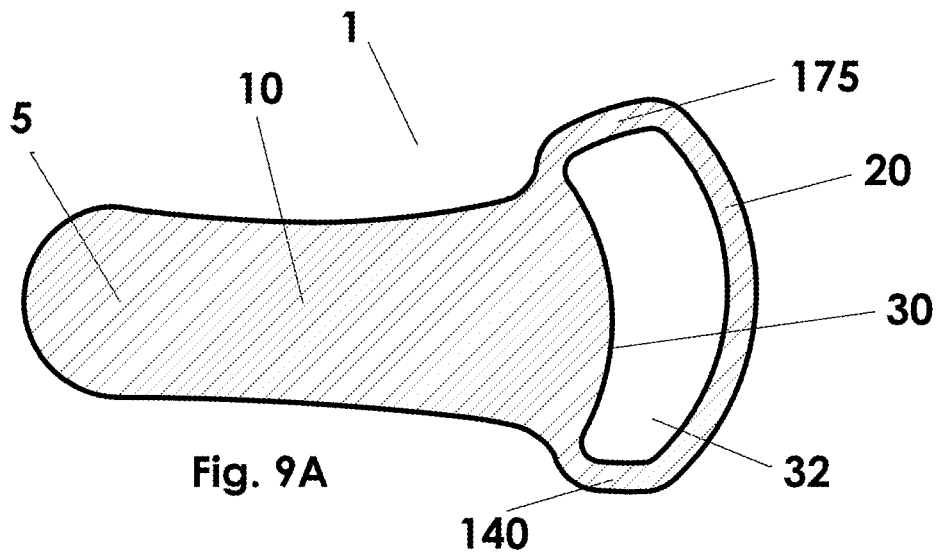
Figure 9B:
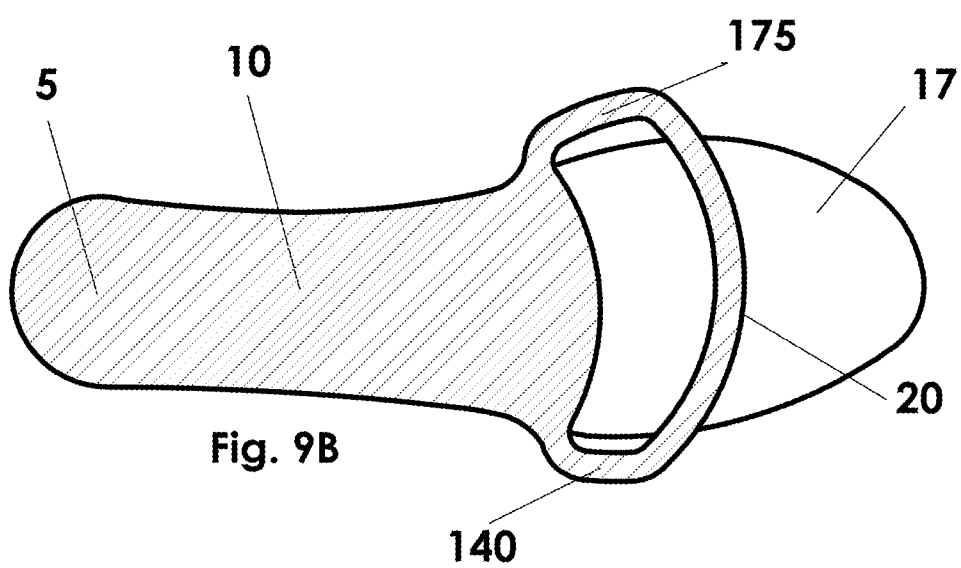
Figure 9C:
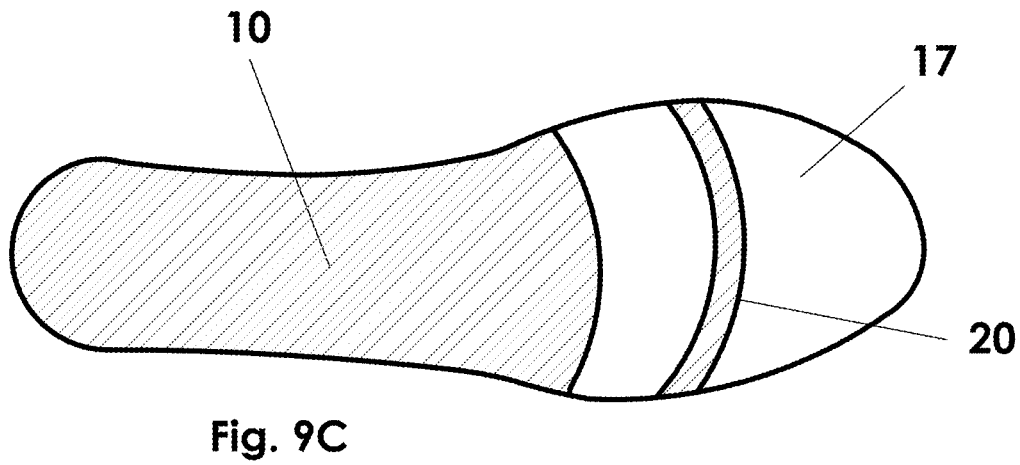

FIGS. 9A, 9B, and 9C depict optional construction stages of an orthotic, and a resulting embodiment of the orthotic resulting from such process.

DETAILED DESCRIPTION

The ensuing description, together with the accompanying figures, makes apparent to a person having ordinary skill in the pertinent art how the teachings of the disclosure may be practiced, by way of non-limiting examples. The figures are for the purpose of illustrative discussion and no attempt is made to show structural details of an embodiment in more detail than is necessary for a fundamental understanding of the disclosure. For the sake of clarity and simplicity, some objects depicted in the figures may not be drawn to scale.

While the figures depict a right foot orthotic, it will be clear that corresponding left foot orthotics are merely mirror images of the depicted right foot figures, and the invention scope extends equally to right and left foot orthotics.

Figure 1:
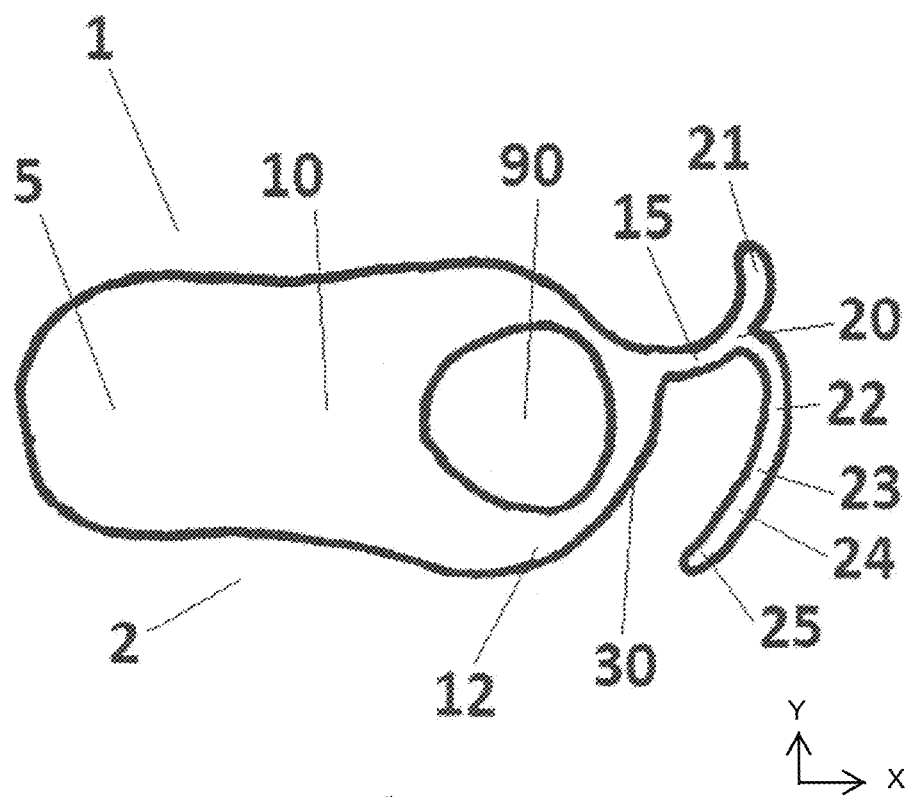
FIG. 1 depicts a top view of a foot orthotic utilizing inter-metatarsal sulcus bar connector.

FIG. 1 depicts a top view of a right foot orthotic 1 according to an embodiment of the invention. The orthotic comprises a body 2 having a heel portion 5 and a midfoot support 10, distal to the heel portion. A forefoot portion 12 extends further distally to the midfoot support 10, the forefoot portion terminating in an orthotic front trimline 30, which defines the end of the orthotic body 2. Commonly, the orthotic front trimline extends operationally to the proximity of the metatarsal heads closer to the heel, however other trimlines are explicitly considered. The heel portion, midfoot support and forefoot portion are preferably integral as a single body.

The exemplary embodiment of FIG. 1 utilizes a single intermetatarsal sulcus bar connector 15 which connects a sulcus support bar 20. The connector is coupled to the front trimline and extends distally therefrom. The connector 15 is disposed to operationally lie between the first and second metatarsal heads. The connector 15 is a generally elongated member having a first end coupled directly or indirectly to the forefoot portion at or about the trimline region, and a second end coupled directly or indirectly to the sulcus bar.

The sulcus support bar 20 depicted in FIG. 1 is coupled to the intermetatarsal connector and extends along an anatomical line defined generally by the foot sulcus. While the sulcus generally extends from the lateral to the medial side of the foot, the sulcus bar may extend along the whole sulcus, or a portion thereof, as required by the anatomical structure to be supported and the desired distribution and translation of the ground reaction forces incurred during walking and standing. In the embodiment depicted in FIG. 1 the sulcus bar 20 may be considered divided to a medial portion and lateral portion. In the embodiment of FIG. 1 the medial portion 21 is coupled to the intermetatarsal connector 15 and extends medially therefrom so as to operationally lie distal to the first metatarsal head. The lateral portion of sulcus bar 20 is coupled to the lateral side of the connector 15 and may be considered to comprise one or more lateral sections. A first lateral section 22 is coupled to the connector 15 and extends laterally therefrom, so as to operationally lie distal to the second metatarsal head. A second lateral section 23 is coupled to the first distal section 22 and extends farther distally therefrom so as to operationally lie distal to the third metatarsal head. Similarly, a third distal section 24 is coupled to the second distal section 23 and extends laterally thereto so as to operationally lie distal to the fourth metatarsal head, and a fourth distal section 25 is coupled to the third distal section 24, and extends laterally thereto so as to operationally lie distal to the fifth metatarsal head. It is noted that in certain embodiments the medial portions of sulcus bar and/or one or more sections distal sections of the sulcus bar may be omitted. FIG. 1 also depicts an optional metatarsal pad 90.

In other embodiments shown herein various sections 22, 23, 24 and 25 of the sulcus bar operationally lie in a similar manner to the manner described for FIG. 1, as applicable.

Figure 2:
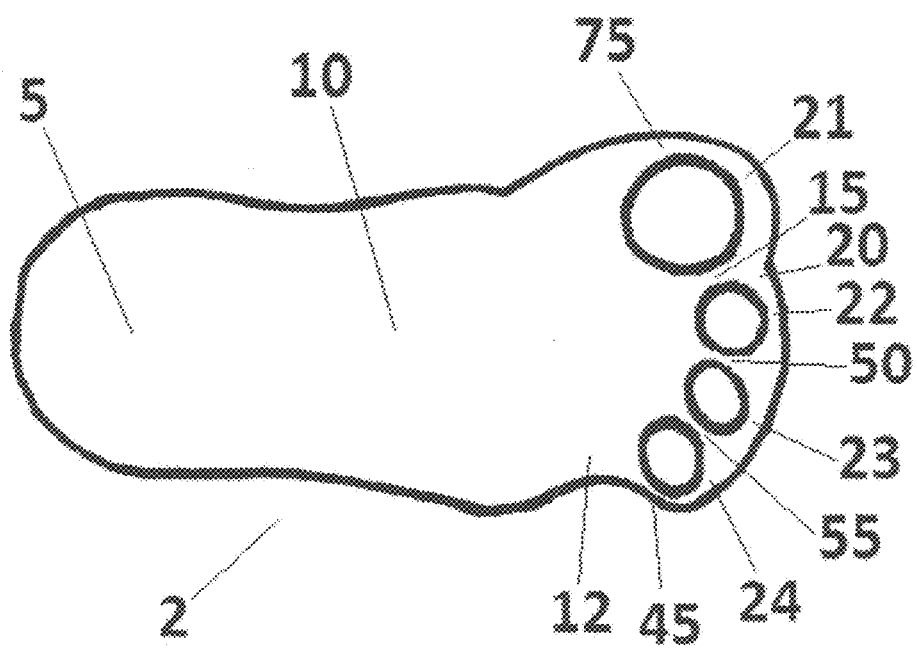
FIG. 2 depicts a top view of a foot orthotic utilizing a plurality of sulcus bar connectors shown without the optional metatarsal pad.

FIG. 2 depicts a top view of an exemplary orthotic embodiment utilizing a plurality of sulcus bar connectors. Similar to other depicted embodiments the orthotic comprises a body 2 having a heel portion 5, a midfoot support 10, and a forefoot portion 12. The embodiment of FIG. 2 features a medial side connector 75 which operationally lie medially to the first metatarsal head, one end of the side connector is coupled to the forefoot portion and extending distally therefrom to couple to a medial portion 21 of the sulcus bar 20. A first 15, second 50 and third 55 and fourth 45 intermetatarsal connectors further couple the sulcus bar to the forefoot section so as to operationally lie between the first and second, second and third, third and fourth, and fourth and fifth metatarsal heads, respectively.

It is noted that in the embodiment depicted in FIG. 2 the most lateral section 25 of sulcus bar 20 which was depicted in FIG. 1 is not shown. This omission is depicted so as to provide but one example of the flexible nature of the invention and its high adaptability to various anatomical needs. It is clear to a person having ordinary skill in the art that the most lateral section 25 may be added if desired. Similarly, other variations depicted in the drawings, as well as other variations that would be clear to the skilled artisan in light of the present disclosure, should be considered to fall under the scope of the invention. By way of example, one or more of the sulcus bar connectors may be removed as desired in order to offer better anatomical support or to increase specific patients' comfort, as long as structural integrity of the orthotic and the relative positioning between the body and the sulcus bar is maintained.

The construction of the embodiment shown in FIG. 2 offers several advantages, including inter alia better positioning of the metatarsal heads, and if the sulcus bar is made sufficiently high the translation of the ground reaction force from the metatarsal heads to the sulcus, as the metatarsal head contact with the surface is minimized and may even be eliminated. The skilled artisan would note that an optional metatarsal pad 90 (not shown in FIG. 2) may further provide ground reaction force distribution. In numerous, but not all, patients, an optimal unweighting arrangement would include both a metatarsal pad, intermetatarsal connectors and the sulcus bar.

Figure 3:
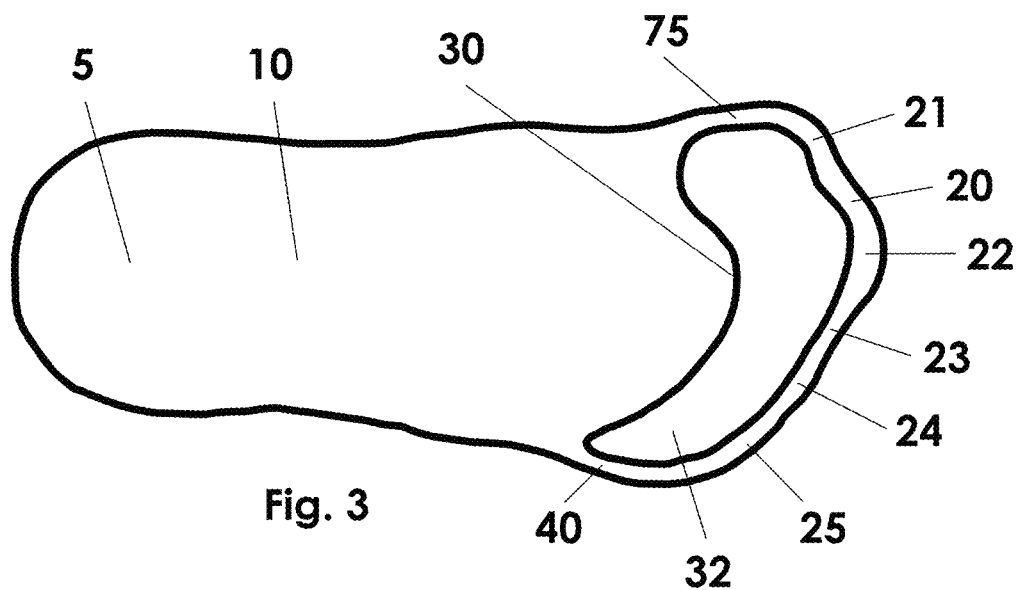
FIG. 3 depicts a top view of a foot orthotic utilizing side sulcus support bar connectors

FIG. 3 depicts a top view of an exemplary embodiment of an orthotic with a sulcus bar supported by two side type sulcus bar connectors namely a medial side connector 75 which operationally lie medially to the first metatarsal head, and a lateral side connectors 40 which operationally lie laterally to the fifth metatarsal head. This arrangement defines a region 32 between the front trimline 30, the proximal side of the sulcus bar 20, and the internal edges of the medial 75 and lateral 40 sulcus bar connectors. The region 32 provides a continuous area for the metatarsal heads to lie in. Such arrangement might be clinically desired for those patients that cannot tolerate intermetatarsal pressure.

Figure 4:
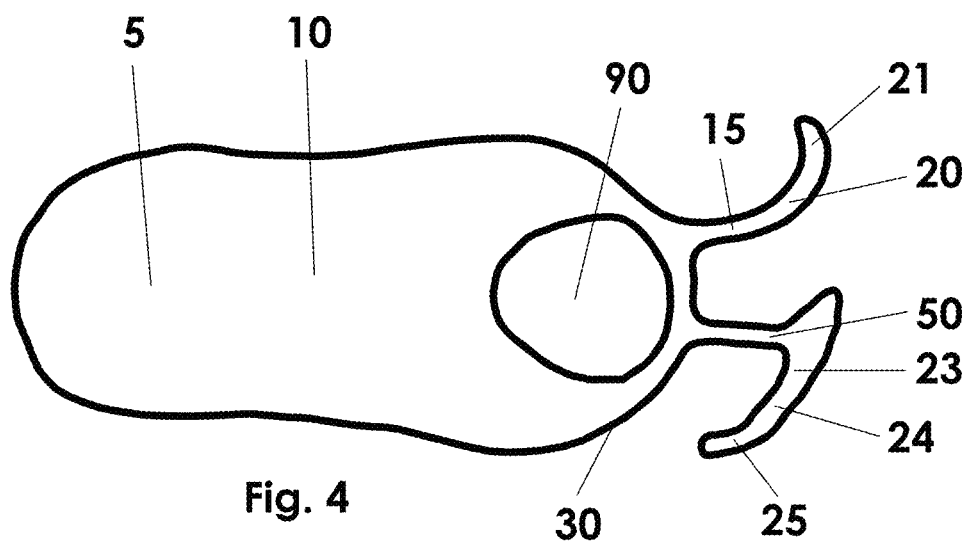
FIG. 4 depicts a top view of a foot orthotic utilizing a plurality of intermetatarsal connectors.

FIG. 4 depicts a top view of yet another exemplary embodiment of an orthotic which utilizes two intermetatarsal sulcus bar connectors, namely 15 which operationally lies between the first and second metatarsal heads, and 50 which operationally lies between the second and third metatarsal heads. This embodiment shows a manner in which the sulcus bar may be constructed with a plurality of physical parts, and/or be discontinuous. In the depicted example, the section of the sulcus bar that was disposed counter to the second metatarsal head enumerated 22 in other figures, is removed. This arrangement may be desirable by way of example, to alleviate personal needs such as an injury or irritation while providing distal support to the other metatarsal heads by the sulcus bar. This embodiment shows again the flexible nature of the invention, and the skilled person would readily recognize other modifications to fit the orthotic according to the invention, to individual needs, and such modification fall under the scope of the invention.

Figure 5:
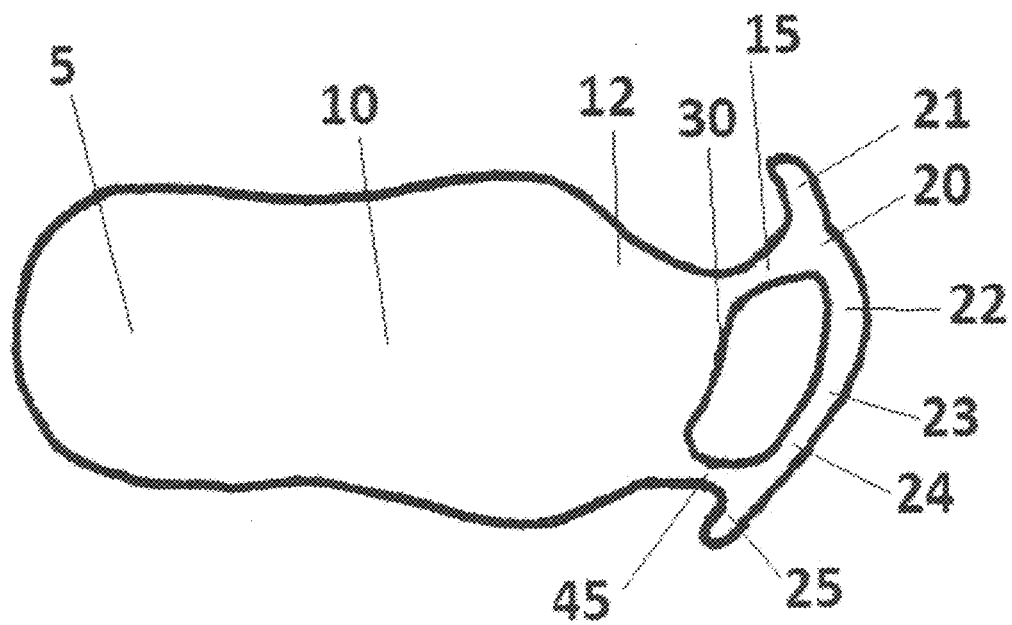
FIG. 5 depicts a top view of yet another embodiment of a foot orthotic utilizing a plurality of intermetatarsal sulcus support bar connectors.

Yet another example of the flexibility and versatility of the present invention is shown in the exemplary embodiment of FIG. 5, which depicts a top view, utilizing a first intermetatarsal connector 15 which operationally lies between the first and second metatarsal heads and a second intermetatarsal connector 45 which operationally lies between the fourth and fifth metatarsal heads. For those cases that present with Morton's neuroma, the area between the third and fourth metatarsal can be particularly sensitive, and this embodiment avoids such pressure.

Figure 6:
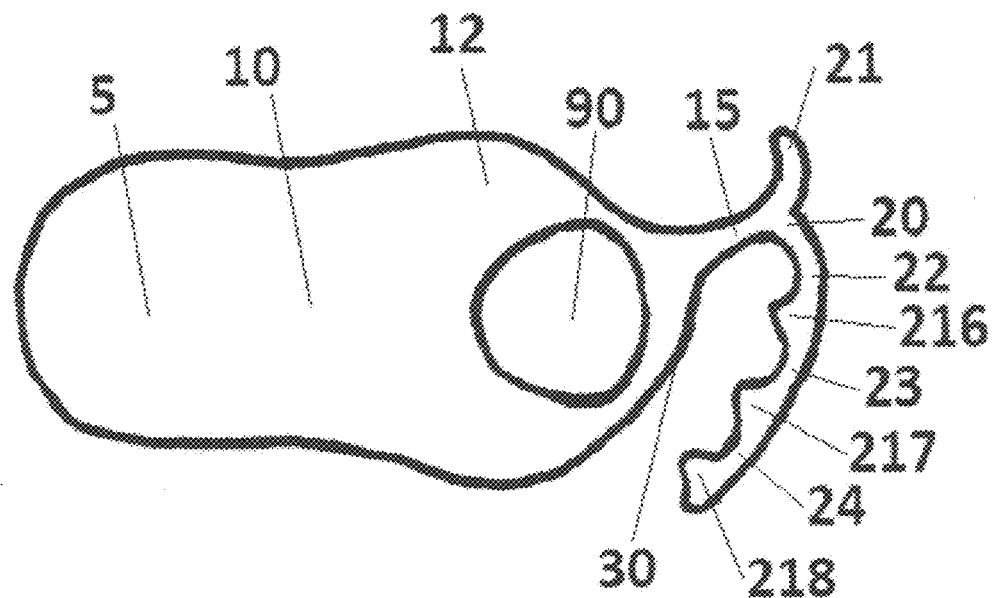
FIG. 6 depicts a top view of an orthotic having a plurality of optional intermetatarsal supports.

FIG. 6 depicts a top view of an orthotic according to an embodiment of the invention which while somewhat similar to the embodiments depicted in FIG. 1, features a plurality of optional Intermetatarsal supports. The lateral section 22 of the Sulcus bar 20 is distal to the second metatarsal head and is connected to an Intermetatarsal support 216 which extends proximally, in the general direction towards the forefoot portion 12. Operationally, the intermetatarsal support 216 is located on the lateral side of the second metatarsal head and the medial side of the third metatarsal head. A second intermetatarsal support 217 is located lateral to the third metatarsal head. The second metatarsal support 217 is also located to the medial side of the fourth metatarsal head. A third intermetatarsal support 218 is at the lateral side of the fourth metatarsal head. The fifth metatarsal head is supported on the medial side by the third intermetatarsal support 218. The depicted embodiment provides an additional unweighting effect to the metatarsal heads. It is noted that the metatarsal pad 90 is depicted in this embodiments, various types of metatarsal pads may be utilized on any of the embodiments of the invention.

Optionally, in any of the aspects and embodiments of the orthotic described above, varying portions of the sulcus bar may have different thickness, both in the distal-proximal direction as well as in the upper-lower direction. By way of example, FIG. 3 shows a section 22 which wider than sections 24 and 25. Similarly, varying portions of the sulcus bar may vary in height, or stated differently, extends upwardly more than other portion(s) of the sulcus bar. By way of example if it is deemed beneficial for the patient to provide increased unweighting of the first metatarsal head relative to the unweighting provided to one or more of the other metatarsal heads, the sulcus bar section 21 which lies distal to the first metatarsal may extend upwardly above the level of sections 22-25, or any other combination. In certain embodiments the sulcus bar tapers, either linearly or stepwise, from a higher medial end to a lower lateral end. The varying height and/or width is carried out when needed to provide better fit for the anatomical need of patients, and such varying height and/or width configurations may be termed a 'thickness' of the sulcus bar at specific positions. FIG. 7A depicts a simplified an elevation projected on the Y-Z plane of an embodiment of the sulcus bar with a variety of heights. In the depicted embodiment a thicker support may be desirable under the first section 21, a less thick section under the second section 22, a still thinner portion under the third section 23, and the sulcus bar is thinnest under the fourth ray 24. The depicted embodiment shows no sulcus support for the fifth metatarsal, however the skilled in the art would readily recognize that such support may be provided when needed by extending the taper of the sulcus bar to the lateral side of the foot. FIG. 7B depicts an elevation projected on the Y-Z plane of an optional embodiment of a sulcus bar having stepwise height variations. While not specifically shown in FIG. 7A or 7B, width-wise variations may take similar approach to the height variations shown in FIG. 7A or 7B along the sulcus bar. Similarly variations in height and/or width may be applied along the length of one or more of the connectors coupling the sulcus bar to the main orthotic body. It is noted that almost universally the sulcus bar will be curved for the specific clinical objectives of the wearer foot anatomy, and the width variation of a curved sulcus bar may be linear or stepwise.

FIG. 8 depicts a simplified flow diagram of a process for manufacturing a foot orthotic incorporating a sulcus bar, the method comprising acquiring 105 a three-dimensional model of a foot of a person, selecting 110 a geometry to provide distal support for at least one metatarsal head of the foot, the forming of the geometry being done utilizing a computer, and form the orthotic by additive printing 120 of an orthotic having the selected geometry.

It is noted that additive printing process greatly simplifies a traditional method manufacturing orthotic which often requires forming an actual model of the foot, followed by manual formation of the desired geometry on the physical model. The modified model is then used for hot-forming a plastic sheet conforming to the model. In contrast, according to aspects of the invention which utilize three dimensional capacity inherent to additive printing the process is greatly simplified, allowing capture of the three dimensional digital model of the patients' foot, editing the resulting model utilizing a computer, and selecting a desired geometry for resolving anatomical abnormalities and/or other desired corrective structure such as size, shape and position of a metatarsal pad and height and other dimensions of an arch support, and the shape and size of a sulcus bar, including any connectors as required. The geometry may be designed utilizing computer software such as Computer Aided Design (CAD) software, and the like. Once a desired geometry befitting the patient is determined, the additive printing process is utilized to form the desired structure in accordance with the geometry, obviating the need for a physical model of the foot. Additionally, this process ensures that the anterior/posterior placement of the sulcus bar is accurately preserved. As the geometry is selected for the patient, the accurate placement of the sulcus bar connector or connectors is also assured, which is of special importance in embodiments where one or more of the connectors extends upwardly to provide support, and to transfer ground forces, to the respective portion of the foot against which it operationally lies.

Optionally, after forming the orthotic having the desired geometry, optional steps such as coating the orthotic or a portion thereof with a topcoating comprising energy absorptive material is optionally performed. Such energy absorptive material may include any combination of foam layer, a fabric layer, or any other resilient covering in order to provide softer interface between the foot or portions thereof and the orthotic. Optionally the orthotic may be affixed to an underlayment layer (not shown) to provide additional mechanical strength and/or support. The underlayment may be formed of an energy absorptive material. In certain embodiments the orthotic is sandwiched between a top and bottom sheets of energy absorptive material. In certain embodiments the top layer of the orthotic is not covered. The to cover and/or bottom underlayment support provide additional mechanical support for the geometrical relationship of the sulcus support bar relative to the orthotic body. It is important to understand that the geometrical relationship between the orthotic body and the sulcus bar, whether set by the connector(s) and/or by the topcover and/or the bottom underlayment layer, all relate to planar geometry on the X-Y plane when the orthotic is at rest. Stated differently, the planar geometrical relationship between the portions of the distal edge and corresponding portions of the sulcus support bar are set by the sulcus bar connector, the topcoat, and/or the bottom support if any of those are utilized, when the orthotic lies without external forces operating thereupon, and the geometrical relationship may be operationally altered such as during dorsiflexion of the toes, and the like.

Trimming, and other desired finishing and dressing steps of the orthotic 150 are commonly taken as a final step of the orthotic. Trimming may include trimming the orthotic itself, the optional bottom underlayment support layer if used, and/or the energy absorbing material, in which it may optionally be enclosed. Finishing may involve smoothing, cleaning and similar steps, such as printing or stamping on the orthosis, if desired.

FIG. 8A provides a simplified flow diagram of certain portions of FIG. 8, and depicts additional optional steps. The step of selecting geometry 110 may be divided to comprise selecting a desired geometry for the main orthotic body 112 and selecting a desired geometry for the sulcus bar geometry 114. In some embodiments the method continues with selection a desired sulcus bar connectors geometry 116 and in other embodiments the process continues with adding geometry for one or fixators 118. In the first case 116 where sulcus bar connectors are utilized, the geometry may be manufactured 120 and orthotic may optionally be coated with the energy absorptive material (not shown), and proceed to the trimming and finishing step 150. Notably, the term selecting may comprise selecting existing geometry, creating a desired geometry, modifying an anatomical geometry, and any combination thereof, as required for customizing the resultant orthotic to the specific benefit of the individual patient for which it is intended.

In a manufacturing method following the construction depicted in FIGS. 9A-C, no connectors are required, but such connectors may optionally be used. At least one fixator is selected and added to the geometry 118 such that it connects the main orthotic body and the sulcus bar, however the fixator is designed so as to at least partially lie outside the outline of the finished orthotic, once covered with the energy absorptive material and/or affixed to the underlayment layer. A plurality of fixators may be utilized. Once the geometry of the main orthotic body, sulcus bar and the connecting fixator is selected, the geometry is manufactured 120, preferably by 3D printing. At least the sulcus bar and the main orthotic body are then geometrically affixed relative to each other 130. As described, affixing the geometrical relationship between the orthotic body and the sulcus bar may be formed and/or assisted by coating of at least portion of both with an energy absorptive material, however commonly all of the top side of both is coated. Alternatively or additionally the affixing may be carried out by affixing the orthotic body and sulcus bar to an underlayment support, and a combination of the underlayment support and the top coating may also be utilized. Notably, the underlayment support may consist of the an energy absorbing material as well. Optionally the fixator(s) need not be covered. Once covered, at least a portion of the fixators is removed 142. The removal may occur as separate step 142 or as a portion of the final trimming and dressing step 150.

FIGS. 9A-C depict an embodiment of an orthosis comprising an orthosis body and a sulcus bar, but without a connector bar connecting the orthosis main body to the sulcus bar. FIG. 9A shows a top view of a right foot orthotic 1 with a medial fixator 175 and a lateral fixator 140 which temporarily couple the main orthotic body to the sulcus bar 20. The fixators are somewhat akin to the medial 75 and lateral 40 connectors as shown in FIG. 3 by way of example, however the fixators are destined to be removed at a later stage, and are thus constructed to extend beyond the outline of the finished orthosis.

FIG. 9B shows the orthotic with an added top cover 17 which extends completely or in part over the main orthotic body and the sulcus bar. Optionally, as shown the top cover 17 further extends beyond to the end of the toes. The top cover commonly comprises energy absorptive material such as closed cell foam. Optionally a bottom underlayment support is also added (not shown). The top cover 17 fixates the sulcus bar disposition relative to the main orthotic body, while the orthosis is at rest. If the optional bottom support is utilized, it cooperates with the top cover to improve spatial stability of the sulcus bar relative to the main orthotic body.

As stated above, flexibility during ambulation is allowed, while maintaining the supportive position of the sulcus bar. FIG. 9C shows the finished orthotic after the fixators have been removed, as they are not needed after the application of the top cover 17. It is noted that FIG. 9B depicts a top cover already trimmed to the desired final dimensions, the top cover may be applied over the fixators as well, and the top cover and the fixators would be trimmed to size at the same step. Alternatively, the fixators may be left uncovered and cut after the application of the top cover.

Finishing and dressing of the final orthotic involves primarily aesthetic and/or minor functional steps, such as scraping, applying insignia, and the like.

It is noted that due to anatomical structure and varying positioning of the foot relative to the orthotic, alignment of the foot portions and the orthotic portions is imprecise and hence the locational correspondence is merely a nominal correspondence. Furthermore, while different elements are described as underlying certain bones, it is further to be understood that soft tissues adjacent to the bone and disposed in-between the bone and the disclosed structure may be ignored for brevity and clarity.

In these specifications the term orthotic, foot orthotic, orthosis, and foot orthosis are used equivalently and interchangeably. Due to some ambiguity in various fields of the art, all the above terms are used to relate to a structurally supportive device for a foot anatomy.

While several sulcus bar sections are described, it is noted that in numerous embodiments the sulcus bar portions are formed integrally as a single body. Moreover, in numerous embodiments, the orthotic body, the sulcus bar connector and the sulcus bar are integrally formed. In integral construction the division between the various component is conceptual rather than physical. However, in some embodiments one of more of those the orthotic components may be formed separately and be connected to each other by glue, melting certain portions together, using various fasteners, and the like.

Unless otherwise specified, relational terms used in these specifications should be construed to include certain tolerances that the skilled in the art would recognize as providing equivalent functionality. Terms such as "about", "generally", and "substantially" in the context of configuration relate generally to disposition, location, or configuration that is either exact or sufficiently close to the location, disposition, or configuration of the relevant element to preserve operability of the element within the invention which does not materially modifies the invention.

In these specifications reference is often made to the accompanying drawings which form a part of the disclosure, and in which are shown by way of illustration and not of limitation, exemplary implementations and embodiments. Further, it should be noted that while the description provides various exemplary embodiments, as described below and as illustrated in the drawings, this disclosure is not limited to the implementations described and illustrated herein, but can extend to other embodiments as would be known or as would become known to those skilled in the art. Reference in the specification to "one embodiment", "this embodiment", "these embodiments", "several embodiments", "selected embodiments" or "some embodiments" means that a particular feature, structure, or characteristic described in connection with the embodiment(s) may be included in one or more implementations, and the appearances of these phrases in various places in the specification are not necessarily all referring to the same embodiment(s). Additionally, in the description, numerous specific details are set forth in order to provide a thorough disclosure, guidance and/or to facilitate understanding of the invention or features thereof. However, it will be apparent to one of ordinary skill in the art that these specific details may not all be needed in each implementation. In certain embodiments, well-known structures, and/or materials have not been described in detail, and/or may be illustrated schematically or in block diagram form, so as to not unnecessarily obscure the disclosure.

For clarity the directional terms such as 'medial', 'lateral', 'anterior', 'posterior', 'proximal', 'distal', 'inferior', 'superior', 'up', 'down', 'left', 'right', and descriptive terms such as 'upper' and 'lower', 'above', 'below', 'sideways', 'inward', 'outward', and the like, are applied according to their ordinary and customary meaning, to describe relative disposition, locations, and orientations of various components. When relating to the drawings, such directional and descriptive terms and words relate to the drawings to which reference is made. Notably, the relative positions are descriptive and relative to the above described orientation such as an orientation which would be exercised during upright walking and/or standing and modifying the orientation would not change the disclosed relative structure. FIG. 1 denotes two axes for reference purposes only, namely X and Y, where X denotes a longitudinal axis and Y denotes the lateral axis. The X and Y axis form a reference X-Y plane for the drawings, and orthotics depicted in the drawings are viewed as projection in accordance with the X-Y plane unless otherwise indicated, such as in FIGS. 7A and 7B. Generally longitudinally distal and/or proximal relationships are viewed along the X axis or substantially parallel thereto, and lateral and medial are viewed along the Y direction of substantially parallel thereto.

Furthermore, these specifications follow to an extent common relative anatomical terminology, such as using the term 'proximal' to describe a location closer to the body core then a "distal" location. The terms "medial" and "lateral" are used similarly to indicate that the medial distance is closer to the midline of the body than the lateral location. Stated differently, and as related to the foot, an item described as "proximal" will be closer to the heel than an item described as being "distal". Similarly an item described as "medial" will be closer to the longitudinal axis of the body, or colloquially to the 'inner' side of the foot while an item described as "lateral" may be colloquially be considered as relating to the 'outer' side of the foot.

It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

I claim:

1. An orthosis for a patient's foot comprising:
   a body portion having a top side and a bottom side, a heel portion, a midfoot portion coupled to and extending distally from the heel portion, and a forefoot portion, coupled to and extending distally from the midfoot portion, the forefoot portion terminating in distal edge distal to the midfoot portion;
   at least one sulcus bar connector having an elongated body with a first end zone coupled to the distal edge, and a second end zone extending distally therefrom, the sulcus bar connector being disposed to operationally lie inbetween any two adjacent metatarsal heads of a patient's foot;

a sulcus support bar coupled to the second end zone and laterally extending upwardly and laterally therefrom;

the orthosis dimensioned to operationally fit under the patient's foot wherein the heel zone or a portion thereof underlies the foot calcaneus, the midfoot zone or a portion thereof underlies the foot arch, the distal edge or a portion thereof underlies an area proximal to the metatarsal heads, and the sulcus bar or a portion thereof laterally underlie at least a portion of the foot sulcus corresponding to at least one proximal phalanx of the foot or a lateral portion thereof.

2. An orthosis as claimed in claim 1, wherein the sulcus bar connector is disposed to operationally [ ] lie between the first metatarsal head and second metatarsal heads.

3. An orthosis as claimed in claim 1, further comprising at least a second sulcus bar connector.

4. An orthosis as claimed in claim 1, further comprising a metatarsal pad disposed adjacent to, or at the distal edge.

5. An orthosis as claimed in claim 1 wherein at least a portion of the orthosis is covered with a topcover.

6. An orthosis as claimed in claim 1, wherein a cross section of at least one portion of the sulcus support bar differs from a cross section of another portion of the sulcus support bar in at least one dimension.

7. An orthosis as claimed in claim 1 wherein at least a portion of the orthosis is manufactured utilizing an additive manufacturing process.

* * * * *